United States Patent [19]
Rydell

[11] Patent Number: 6,007,474
[45] Date of Patent: Dec. 28, 1999

[54] RADIOACTIVE AND/OR THERMAL SEED IMPLANTATION DEVICE

[75] Inventor: Mark A. Rydell, Golden Valley, Minn.

[73] Assignee: Ablation Technologies, Inc., San Diego, Calif.

[21] Appl. No.: 08/954,155

[22] Filed: Oct. 20, 1997

[51] Int. Cl.⁶ ................................................. A61M 36/00
[52] U.S. Cl. .............................. 600/7; 604/57; 604/59; 604/61; 604/62
[58] Field of Search .......................... 600/1, 3, 7; 604/57, 604/59, 61, 62, 63, 64, 93, 95

[56] References Cited

U.S. PATENT DOCUMENTS

| | | | |
|---|---|---|---|
| 2,269,963 | 1/1942 | Wappler | 600/7 |
| 4,402,308 | 9/1983 | Scott . | |
| 4,700,692 | 10/1987 | Baumgartner . | |
| 4,763,671 | 8/1988 | Goffinet . | |
| 5,135,493 | 8/1992 | Peschke | 604/62 |
| 5,147,295 | 9/1992 | Stewart | 604/61 |
| 5,242,373 | 9/1993 | Scott et al. . | |
| 5,429,583 | 7/1995 | Paulus et al. . | |

FOREIGN PATENT DOCUMENTS 5-49704   3/1993   Japan .

*Primary Examiner*—Linda C. M. Dvorak
*Assistant Examiner*—Rosiland Kearney
*Attorney, Agent, or Firm*—Nikolai, Mersereau & Dietz, P.A.

[57] ABSTRACT

An instrument for implanting radioactive and/or thermal seeds in body tissue for radiation and/or heat therapy comprises a tubular hypodermic needle barrel affixed to a pistol-grip shaped handle incorporates a reciprocally movable push rod for stripping one such seed from a cartridge containing a plurality of seeds and advancing it to the end of the barrel. Actuation of a trigger in the pistol grip handle causes the barrel to retract relative to the push rod, causing the seed to be deposited in the channel in the body tissue created by the original puncturing thereof by the instrument's barrel.

6 Claims, 4 Drawing Sheets

RADIOACTIVE AND/OR THERMAL SEED IMPLANTATION DEVICE

BACKGROUND OF THE INVENTION

1. Field of the Invention

This invention relates generally to a surgical instrument useful in injecting thermal and/or radioactive seeds percutaneously into a body organ, and more particularly to an instrument of the type described which is effective to deposit such seeds in a desired axial alignment.

2. Discussion of the Prior Art

In the Paulus et al. U.S. Pat. No. 5,429,583, there is described a seed of a ferromagnetic material which when injected into body tissue and subsequently exposed to an oscillating magnetic field produces localized heating of the tissue surrounding the seed for therapeutic purposes. For example, if the seeds are injected into the prostate gland, the heating may be used to shrink the prostate gland in addressing BPH. Radioactive seeds have also been injected into tumorous tissue so that the resulting radiation given off by the seeds will destroy the cancerous tissue.

Pending application Ser. No. 08/864,486, filed May 28, 1997, describes a method for manufacturing a combination ferromagnetic/radioactive seed whereby both radioactive emissions and heat can simultaneously be applied to selected tissue structures.

When it is considered that to achieve optimum magnetic coupling between implanted ferromagnetic seeds and an external magnetic field producing coil, there must be appropriate alignment of the applied field to the implanted seeds, an instrument is required that can be used to inject such seeds so as to be aligned along a desired axis so that the patient's body can be appropriately oriented with respect to the external field coil.

The Scott U.S. Pat. Nos. 4,402,308 and 5,242,373 describe medical instruments for percutaneously injecting radioactive seeds into tumorous tissue. Generally, they comprise a tubular hypodermic needle into which radioactive seeds may be fed. A push rod is provided for effectively forcing the seeds out of the distal end of the tubular needle. However, the device tends to be difficult to manipulate and often results in misaligned seeds following their implantation.

Thus, a need exists for an instrument that allows precise deposition of thermal/radioactive seeds into body tissue with the seeds being aligned with a predetermined axis.

SUMMARY OF THE INVENTION

In accordance with the present invention there is provided an improved apparatus for implanting ferromagnetic and/or radioactive seeds in body tissue. The apparatus includes a pistol-grip shaped handle having a spring-loaded trigger member supported in the handle. Projecting from the pistol-gripped shaped handle is a tubular barrel having a proximal end, a distal end and a lumen extending therebetween. The distal end of the barrel is beveled and honed to facilitate penetration through the skin and into underlying body tissue. The pistol-gripped shaped handle also supports a cartridge that holds at least one, but preferably a plurality, of ferromagnetic and/or radioactive seeds each of a predetermined length in axial alignment with the lumen of the barrel. Means are provided for advancing the bottommost one of the seeds out of the cassette and along the lumen of the barrel to the distal end thereof. When the spring-loaded trigger is squeezed, the barrel is retracted in a proximal direction through a distance corresponding to the length of the selected seed causing it to be expelled from the lumen of the barrel and deposited in body tissue in a channel that had resulted from the penetration of the barrel into the body tissue to be treated. Upon each actuation of the spring-loaded trigger, the barrel retracts one seed length, depositing yet another seed in the tunnel created by the penetration of the barrel through the body tissue.

DESCRIPTION OF THE DRAWINGS

The foregoing features, objects and advantages of the invention will become apparent from those skilled in the art from the following detailed description of a preferred embodiment of the invention in which like numerals in the several views refer to corresponding parts.

DESCRIPTION OF THE PREFERRED EMBODIMENT

Figure 1:
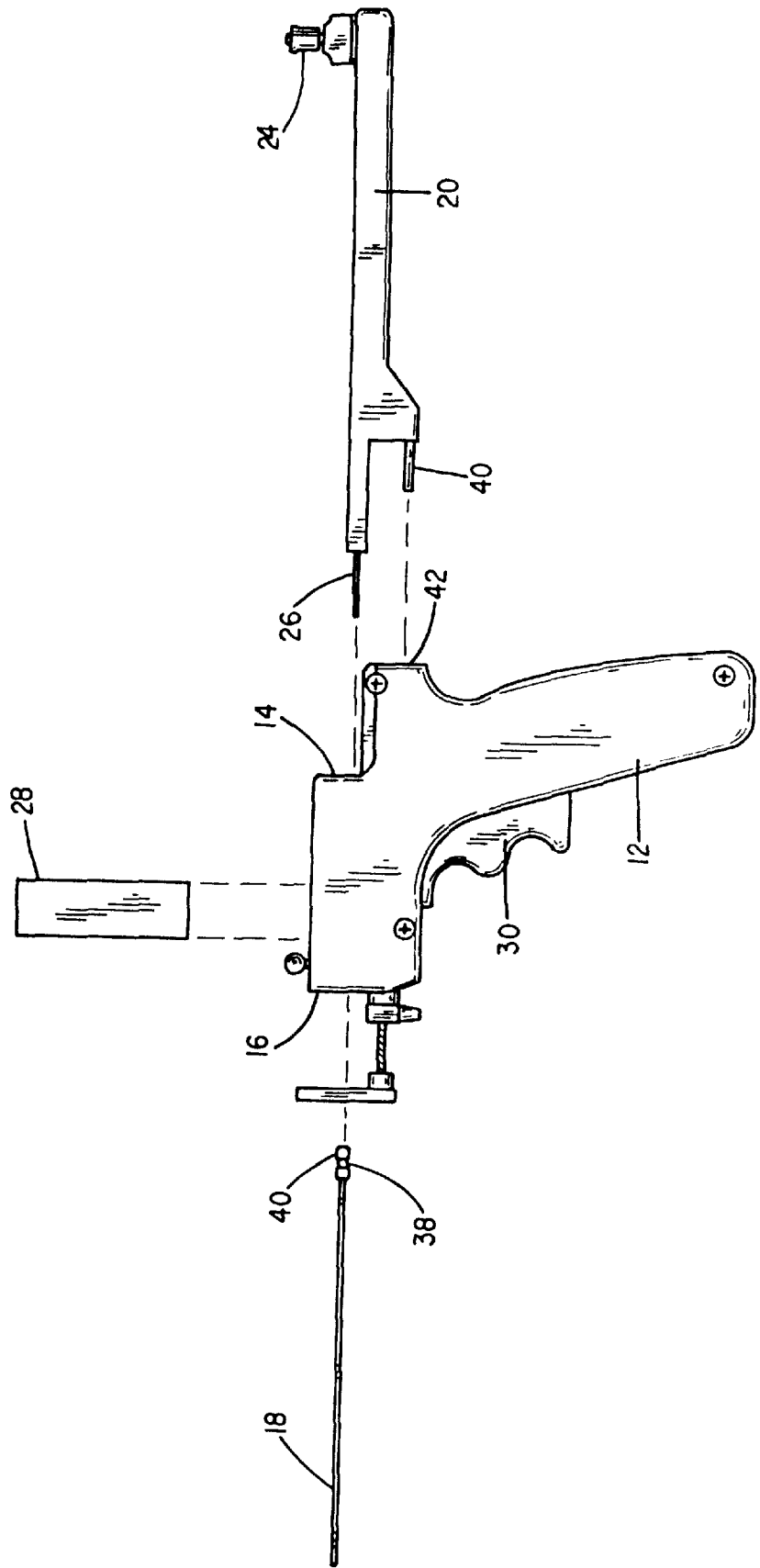
FIG. 1 is an exploded view of the seed injection device comprising a preferred embodiment of the invention.

Referring to the drawings, the instrument comprising the preferred embodiment of the present invention is indicated generally by numeral 10 and is seen to include a pistol-grip shaped handle 12 having a proximal end 14 and a distal end 16. Removably attached to the handle 12 and projecting outwardly from the distal end 16 thereof is a tubular barrel member 18, preferably fabricated from hypodermic needle stock. The internal lumen of the tubular barrel 18 has a diameter slightly larger than the diameter of the seeds to be implanted.

Figure 2:
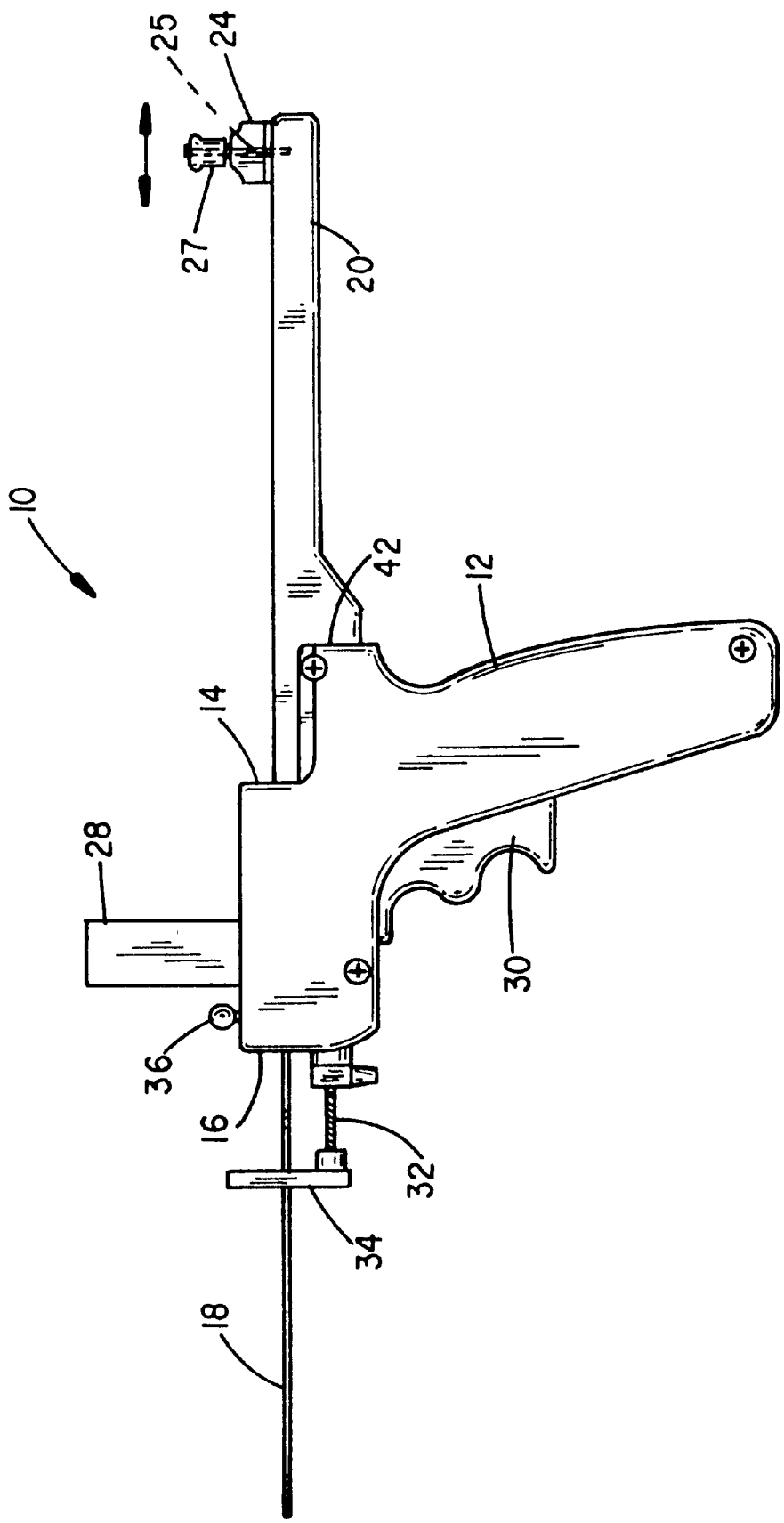
FIG. 2 is a side elevational view of the instrument in assembled form.
Figure 3:
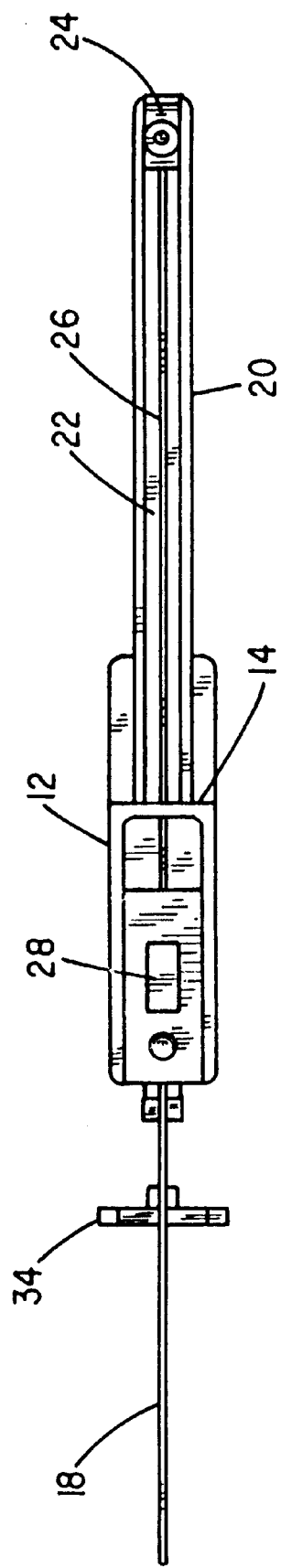
FIG. 3 is a top elevational view of the instrument.

The handle member 12 also supports a molded plastic guide 20 and visible in the view of FIG. 3 there is a channel 22 in which is fitted a slide member 24 for reciprocal longitudinal movement as indicated by the doubled-headed arrow in FIG. 2. The slide 24 has a spring-loaded detent pin 25 affixed to a gripping knob 27 for engaging an aperture formed at a distal end of guide 20. The knob 27 must be raised to release the slide before it can be pulled rearward, i.e., proximally. An elongated wire push rod 26 is affixed to slide member 24.

Supported atop the handle 12 is a seed cartridge 28 which when filled, contains a plurality of the seeds to be injected through the skin and into target body tissue to be treated.

Also supported in the pistol-grip shaped handle 12 is a spring-loaded trigger member 30. As will be explained in greater detail, the trigger 30 is operatively coupled to a threaded rod 32 that projects in the distal direction from the distal end 16 of the handle 12 and affixed to the distal end of the rod 32 is a U-shaped stop member 34.

Figure 4:
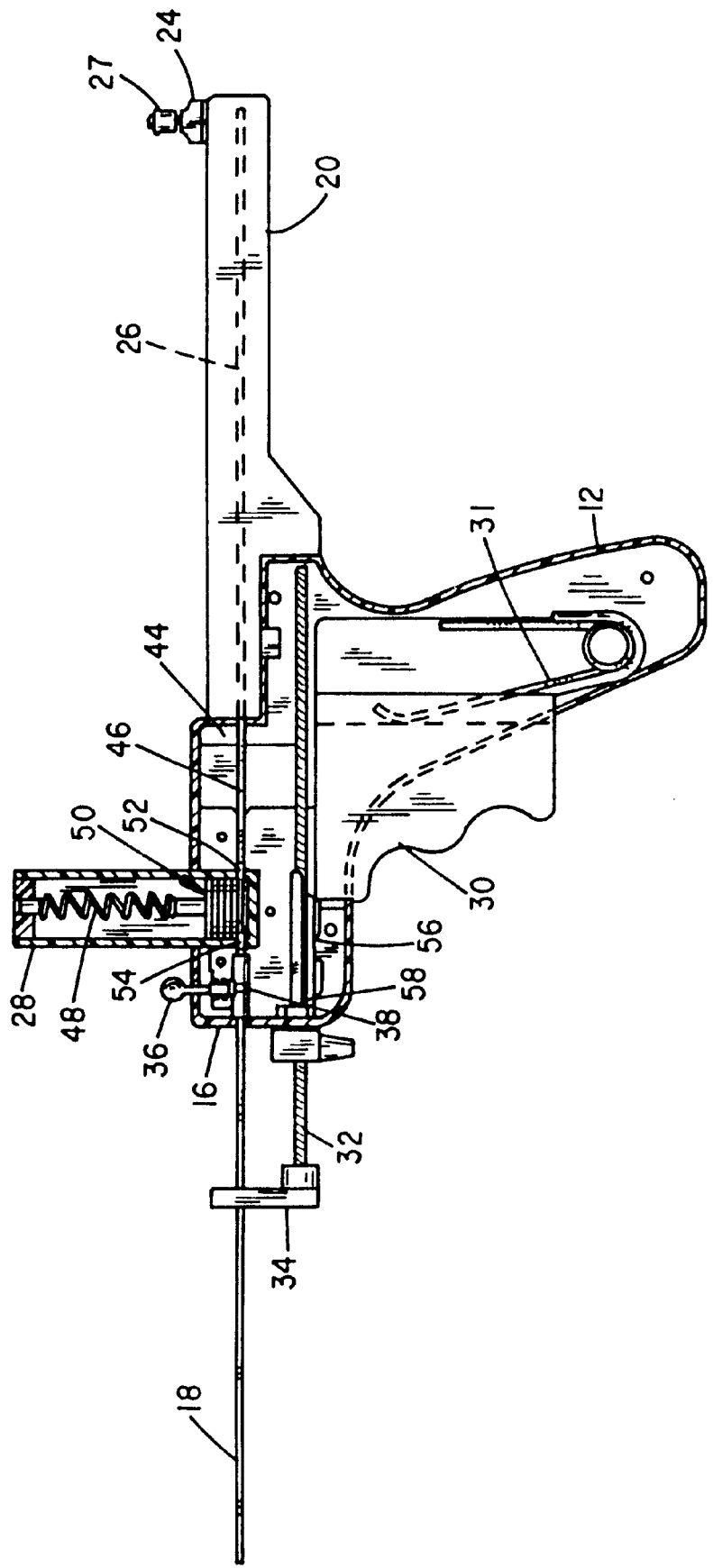
FIG. 4 is a partially sectioned side elevational view showing the internal working parts of the handle.

Referring to FIGS. 1 and 4, the barrel 18 attaches to the handle 12 in a releasible fashion by means of a spring-loaded detent pin 36, the lower end of which is adapted to fit into an annular groove or recess 38 formed into the exterior of a tubular stud 40 that is affixed to the proximal end of the hypodermic needle barrel 18. Lifting of the detent pin 36 permits the hub and barrel to be withdrawn out through an opening formed through the distal end face 16 of the handle.

In the exploded view of FIG. 1, there is shown one of a pair of alignment pins 40 that project outward in a distal direction from a face of the guide 20 and these alignment pins are designed to fit into mating bores (not shown) formed on a proximal edge 42 of the handle 12. When so inserted, the push rod 26 becomes longitudinally aligned with bores 44 and 46 (FIG. 4) formed in the handle.

With continued reference to FIG. 4, it can be seen that the seed cartridge 28 comprises a box-like housing containing a spring-loaded plunger 48 that acts against a plurality of rod-shaped seed implants indicated generally by numeral 50. The force of the spring 48 causes a bottommost one of the seeds 50 in the stack to become aligned with bores 52 and 54 formed in opposed parallel walls of the cartridge 28. The bores are dimensioned and positioned such that movement of the push rod 26 in the distal direction will strip the bottommost seed from the stack, forcing it through the lumen of the hub 40 and down the lumen of the tubular barrel 18.

With reference to FIG. 3, the length of the push rod 26 relative to that of the barrel 18 is such that when the slide 24 is advanced fully against the distal end 14 of the handle and the detent pin 25 falls into an aperture located near the proximal end 14 of the handle 12, the end of the push rod will be one seed length from the distal end of the barrel 18.

As can be seen in FIG. 4, affixed to the trigger 30 is a flat spring metal pawl 56 that is adapted to engage the threads on the rod 32. A similar flat spring metal pawl 58 is affixed to the handle 12 and its free end is also adapted to engage the threaded rod 32.

In use, the physician will place a cartridge 28 containing a plurality of seeds 50 to be implanted into a receptacle in the handle. A tubular barrel 18 and a guide 20 with a push rod 26 will be selected as a matched pair, possibly with color coding or the like to insure that the two will be used together. The length thereof are selected to accommodate the physiology of the patient, especially the distance from the patient's skin surface to the target tissue. The barrel member 18 is inserted into the handle by lifting the detent pin 36 and then inserting the hub 40 through the distal face 16 of the handle until the detent groove 38 "clicks" with the detent pin. The selected guide and push rod assembly 20 corresponding to the barrel length is then plugged into the proximal side of the handle and the slide 24 is advanced in the distal direction so that the leading end of the push rod 26 passes through the aligned bores 52 and 54 in the cartridge, stripping off the bottommost seed and advancing it through the bore of the hub 40 and down the barrel 18. The barrel 18 is then advanced percutaneously into the target tissue where seeds are to be implanted.

Next, by holding the stop 34 against the patient's body or against a positioning template affixed to the operating table or a rectal ultrasound probe closely adjacent to the patient's anatomy where the seeds are to be injected and first squeezing and then releasing the trigger 30, because the stop 34 cannot itself move forward, the handle assembly and attached barrel will be caused to move proximally along the threaded shaft 32, resulting in the seed at the end of the barrel being released from the barrel and held in the puncture in the target tissue. The slide knob 24 may then be lifted to release it and manually retracted in its guide 22 and then again advanced to strip the next seed from the cartridge 28 and advance it through the barrel 18 to its distal end where again squeezing and releasing the trigger 30 will cause that next seed to be released near the tail end of the preceding seed in the same puncture wound.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. For example, the instrument can be further automated by incorporating pinch rollers driven by a battery driven by a small D.C. motor to actuate the reciprocal movement of the push rod 26 each time the trigger 30 is squeezed to thereby load a new seed in the hypodermic needle barrel 18.

What is claimed is:

1. Apparatus for implanting ferromagnetic seed of a predetermined length dimension in body tissue at regularly spaced intervals along a predetermined longitudinal axis, comprising:

(a) a pistol-grip shaped handle having a spring-loaded trigger member supported in said handle;

(b) a tubular barrel having a proximal end, a distal end and a lumen extending therebetween, the distal end of the barrel being sharpened for penetration into the body tissue along the predetermined longitudinal axis;

(c) a cartridge holding at least one ferromagnetic seed in alignment with the lumen of the barrel at the proximal end thereof;

(d) first means mounted on the handle for initially advancing the at least one seed out from the cartridge and through the lumen such that a leading end of the at least one seed is at the distal end of the barrel;

(e) second means actuated upon squeezing of the spring-loaded trigger member for retracting the barrel relative to the handle in a proximal direction from a home position a distance equal to said predetermined length dimension to thereby release the at least one seed from the distal end of the barrel in alignment with the predetermined longitudinal axis;

(f) third means actuated upon release of the spring-loaded trigger member for displacing the pistol grip handle in a proximal direction by a distance corresponding to said predetermined length dimension as the barrel returns to said home position.

2. The apparatus of claim 1 wherein the first means comprises a second slide member affixed to the handle with a push rod disposed in the second slide member for reciprocating longitudinal motion there along, the push rod having an operating length generally equal to the length of the barrel less the predetermined length dimension of the at least one seed.

3. The apparatus of claim 1 wherein the second means comprises a first slide member disposed on the handle and coupled to the spring-loaded trigger, the slide member supporting the barrel and the cartridge independent of the first means.

4. The apparatus of claim 1 wherein said cartridge comprises a rectangular box-shaped housing adapted to contain a plurality of seeds stacked in parallel vertical relating to one another, the cartridge including a pair of aligned apertures in opposed parallel walls of the housing in alignment with the lumen of the barrel, the push rod being dimensioned to fit through the pair of aligned apertures during its reciprocal longitudinal motion.

5. The apparatus of claim 1 wherein the third means comprises a ratchet rod supported in the handle, the ratchet rod having a stop member at a distal end thereof, and a pawl affixed to the spring-loaded trigger member for cooperating with the ratchet rod, release of the spring-loaded trigger with the stop member abutting a stationary object resulting in said proximal displacement of the pistol grip handle.

6. The apparatus of claim 5 wherein each actuation and release of the spring-loaded trigger displaces the distal end of the barrel a distance corresponding to said predetermined length dimension along said longitudinal axis.

* * * * *